United States Patent [19]

Berkowitz

[11] 3,969,352

[45] July 13, 1976

[54] CRUDE CYANURIC ACID PURIFICATION

[75] Inventor: Sidney Berkowitz, Highland Park, N.J.

[73] Assignee: FMC Corporation, Philadelphia, Pa.

[22] Filed: Oct. 2, 1974

[21] Appl. No.: 511,447

[52] U.S. Cl. .................................................. 260/248 A
[51] Int. Cl.² ........................................... C07D 251/32
[58] Field of Search ................................. 260/248 A

[56] References Cited
UNITED STATES PATENTS

| | | | |
|---|---|---|---|
| 3,357,979 | 12/1967 | Sobocinski et al. | 260/248 |
| 3,644,359 | 2/1972 | Mesiah et al. | 260/248 |
| 3,761,474 | 9/1973 | Mesiah | 260/248 |

*Primary Examiner*—John M. Ford

[57] ABSTRACT

Process for purifying crude cyanuric acid whereby crude cyanuric acid is digested with a mono-substituted salt of a dibasic or tribasic inorganic acid at a temperature of about 160°C to about 220°C under at least the autogenously developed pressure to digest the crude cyanuric acid. A novel, large, free-flowing cyanuric acid product is recovered free of any hard cement-like masses.

45 Claims, No Drawings

CRUDE CYANURIC ACID PURIFICATION

This invention relates to the formation of cyanuric acid and to the purification of crude cyanuric acid with a mono-substituted salt of a dibasic or tribasic inorganic acid at high temperatures. This invention also relates to the formation of novel, free-flowing cyanuric acid crystals.

Cyanuric acid has the empirical formula $C_3H_3O_3N_3$ and is the main product produced by heating urea, biuret or mixtures of both in a kiln at temperatures of about 200° to 350°C. Unfortunately, the product produced is composed of only about 75% to 80% cyanuric acid with the remainder of the product containing impurities such as amino substituted triazines. The amino substituted triazine impurities generally contain about 25% ammelide and minor amounts of other impurities such as ammeline. The cyanuric acid product mixture is conventionally referred to as crude cyanuric acid. Since it is quite difficult to separate the crude cyanuric acid into its component parts in order to recover pure cyanuric acid, various methods have been proposed to purify the cyanuric acid by converting the triazine impurities into cyanuric acid by acid hydrolysis. This conversion by acid hydrolysis is sometimes referred to as the acid digestion process.

The acid digestion process comprises mixing crude cyanuric acid with a strong mineral acid to give a slurry containing 10% to 15% undissolved solids. The mineral acids disclosed as being operative are sulfuric, hydrochloric, nitric and phosphoric acid, with sulfuric acid being preferred. The slurry is digested at reflux temperatures (about 104°C) for 1 to 10 hours. This digestion in hot mineral acid results in the hydrolysis of most of the triazine impurities to cyanuric acid. Methods employing this procedure are described in U.S. Pat. Nos. 2,943,088 and 3,107,244. Higher temperatures, up to about 130°C, may be employed if superatmospheric pressures up to 100 p.s.i. are employed. See U.S. Pat. No. 3,107,244. The use of temperatures above 165°C has also been suggested with strong mineral acids, such as sulfuric acid, in U.S. Pat. No. 2,768,167.

Because the acid digestion process involves heating and mixing a thick slurry of solids in a digester vessel for long periods of time, some problems are encountered. Mixing in the digester vessel is often difficult and a constant build-up of solids on the walls of the digester results. Frequently, large chunks of this solid build-up break away from the walls and either plug the exit lines or bend the agitator. Furthermore, strong mineral acid reaction mixtures held at operating temperatures for prolonged periods can result in partial hydrolysis of the cyanuric acid to ammonia and carbon dioxide, thus decreasing cyanuric acid yields.

Additional problems result when hydrochloric acid or phosphoric acid have been employed at conventional operating temperatures rendering the use of either of these acids commercially impractical. Commercial operation of a hydrochloric acid digestion process is extremely difficult and hazardous and results in many shut downs because of equipment breakdown and corrosion. Commercial operation of a phosphoric acid digestion process at conventional operating temperatures has not been possible because of the slow impurity conversion rate and because the cyanuric acid is partially hydrolyzed to ammonia and carbon dioxide over the prolonged digestion period. Furthermore, the reaction rate with phosphoric acid is approximately five times slower than with strong mineral acids, such as sulfuric acid.

The sulfuric acid and nitric acid digestion processes, while being commercially effective processes when carried out at temperatures up to 130°C, have caused numerous pollution problems with regard to the separated acid digestion solution. The separated acid digestion solution has been partially or entirely discarded as an untreated waste stream since treatment to render them safe for discharge is difficult and expensive. Untreated acid digestion solutions discharged into natural waterways, however, disrupts and often destroys natural fauna and flora. Commercial operation of a sulfuric acid digestion process at temperatures above 165°C is extremely difficult and hazardous and would result in extensive equipment corrosion over a short period of time.

In addition to the above acid digestion process deficiencies, the cyanuric acid product produced by conventional processes is often difficult to separate from the acid digestion solution and difficult to handle once separated because of the small crystals produced. The crystals generally have particle sizes between about 30 and 100 microns. Crystals of this size must be filtered carefully to prevent valuable cyanuric acid crystals from passing through conventional separating means along with the filtrate.

It has been unexpectedly discovered that crude cyanuric acid can be purified, by mixing in water sufficient amounts of crude cyanuric acid and a mono-substituted salt of an inorganic acid, wherein the inorganic acid is a dibasic or tribasic inorganic acid, to form a 10% to 45% crude cyanuric acid slurry containing about 10% to about 30% of said monosubstituted salt of an inorganic acid, heating the slurry to a temperature of about 160°C to about 220°C under at least the autogenously developed pressure to digest the crude cyanuric acid impurities, cooling the digested cyanuric acid slurry to precipitate the cyanuric acid crystals, and recovering the cyanuric acid crystals from the digestion solution.

The process of this invention permits the purification of crude cyanuric acid in a commercially simple and efficient manner without the concomitant metal corrosion problems associated with the prior art methods and without the need for large expensive digester reactors. It permits the recovery of cyanuric acid in exceptionally high yields and exceptionally high purities in relatively short periods of time, that is between 15 seconds and 10 minutes. It unexpectedly results in the formation of a cyanuric acid product which contains at least 90% cyanuric acid crystals having particle sizes between 700 and 800 microns. It permits the use of the discharged digestion solution as a source of useful by-product as well as the direct discharge of the digestion solution into effluent waste streams without prior treatment, not heretofore possible.

The use of a mono-substituted salt of a dibasic or tribasic acid to purify crude cyanuric acid in high yields at high reaction temperatures, and in relatively short reaction periods is highly unexpected. It is unexpected because these salts are relatively weak acids as compared to the fully dissociable strong mineral acids conventionally employed, such as sulfuric acid, hydrochloric acid, and nitric acid.

In the process of this invention, crude cyanuric acid containing ammelide and other amino-substituted triazine impurities such as melamine, ammeline, and ammeline:ammelide complexes, are mixed with a mono-substituted salt of a dibasic or tribasic inorganic acid. The mono-substituted salt of said inorganic acid dissolves all acid-soluble impurities present in the reaction mixture. It hydrolyzes ammelide and the other triazine impurities to cyanuric acid and a corresponding ammonium salt. Alternately, ammelide, melamine, ammeline or ammeline:ammelide complexes are mixed either separately or in combination with the mono-substituted salt of said inorganic acid and treated according to the process of the invention to yield cyanuric acid.

The crude cyanuric acid is employed in amounts sufficient to produce a crude cyanuric acid slurry. The crude cyanuric acid slurry concentration is not critical. However, from a commercial process standpoint, slurry concentrations below about 10% or above about 45% are not desirable. Slurry concentrations below about 10% are not economical in view of the small cyanuric acid concentrations treated. Slurry concentrations above about 45% are not workable because they are difficult to handle. Accordingly, crude cyanuric acid slurry concentrations between 10% and 45% are employed, with slurry concentrations between 10% and 25% being preferred.

The mono-substituted salts of a dibasic or tribasic inorganic acid employed in this invention either singly or in combination are preferably ammonium bisulfate ($NH_4HSO_4$), sodium bisulfate ($NaHSO_4$), potassium bisulfate ($KHSO_4$), ammonium dihydrogen orthophosphate ($NH_4H_2PO_4$), sodium dihydrogen orthophosphate ($NaH_2PO_4$), and potassium dihydrogen orthophosphate ($KH_2PO_4$) including the hydrates of these salts. Other less preferred but equivalent salts may also be employed. Some of the latter salts include lithium, rubidium and cesium bisulfates or dihydrogen orthophosphates, as well as other equivalent inorganic acids capable of forming a salt containing the acid radical and one or more hydrogen atoms. Ammonium bisulfate and ammonium dihydrogen orthophosphate are the most preferred salts since ammonia is a by-product from the hydrolysis of the amino-substituted triazines and these salts would be most compatible with this by-product.

The salt must be employed in sufficient amounts to hydrolyze the amino-substituted triazines. This amount must be at least stoichiometrically equivalent to the amino-substituents on the triazine ring compound. Accordingly, one mole of salt will hydrolyze one mole of ammelide which contains one amino group. Two moles of salt will hydrolyze one mole of ammeline which contains two amino groups. Three moles of salt will hydrolyze one mole of melamine which contains three amino groups. If there is not an equivalent amount of salt present, the reaction does not go to completion. For optimum results the amount of salt should be at least 10% over the stoichiometric amount. To obtain at least stoichiometric amounts of the salt it is preferred to mix the crude cyanuric acid with sufficient amounts of salt so that the resulting slurry contains 10% to 45% crude cyanuric acid and about 10% to about 30% salt. Salt concentrations above about 30% may be employed, but are not preferred. Salt concentrations above about 30% will not increase the amino-substituted triazine hydrolysis rate and will result in the coprecipitation of the salt when the cyanuric acid crystals are precipitated necessitating additional purification procedures to obtain a pure cyanuric acid product.

The crude cyanuric acid slurry is obtained by either mixing dry crude cyanuric acid and the mono-substituted salt in water, or mixing aqueous solutions of one or both of these materials together.

Digestion of the crude cyanuric acid impurities must be carried out at a pH below about 5.0 and preferably between 0.2 and 5.0, and most preferably between 0.5 and 2.5. At pH's above about 5.0 the hydrolysis reaction essentially ceases. These pH's are obtained when salt concentrations from about 10% to about 30% are employed to digest the crude cyanuric acid.

Digestion of the crude cyanuric acid slurry must be carried out at a temperature of about 160°C to about 220°C. At temperatures of about 160°C to about 220°C the reaction rate is very rapid and substantially all of the amino-substituted triazines are converted to cyanuric acid. At temperatures below about 160°C, the reaction rate is slow, and the amount of amino-substituted triazines converted to cyanuric acid is significantly decreased. At temperatures above about 220°C, the mono-substituted salts catalyze the thermal decomposition of cyanuric acid, thus substantially decreasing cyanuric acid yields. Optimum reaction rate and optimum conversion rate occurs at the preferred temperature of about 190°C to about 205°C.

Digestion of the crude cyanuric acid slurry must be carried out under pressure in order to prevent water vaporization losses. The pressure, however, is not critical and the autogenously developed pressure, that is the pressure developed in the system, at the various reaction temperatures is normally used. Generally, the autogenously developed pressure will vary from about 130 to about 275 p.s.i.g. at reaction temperatures of about 182°C to about 217°C respectively.

The time period required for the reaction to be maintained at the desired operating temperature is not critical. Once the reaction mass reaches the particular operating temperature, the amino-substituted triazines immediately begin forming cyanuric acid. Maximum conversion, that is over 90%, of the amino-substituted triazines to cyanuric acid is obtained in reaction times of about 15 seconds to about 10 minutes, even though reaction times longer than 60 seconds have not significantly increased the percentage of triazines converted. However, from a commercial standpoint, reaction times up to about 10 minutes and preferably 1 to 5 minutes are employed when conventional pressure reactors are used. Shorter reaction times, that is reaction times up to 60 seconds, are commercially feasible with commercially available pipe reactors. A pipe reactor is an elongated tubular reaction chamber wherein the feed enters the reactor in one end and exits out the other end. The reaction takes place within the tube which is heated by external sources. Use of pipe reactors greatly increases the production of purified cyanuric acid and eliminates the need for large, expensive reactors currently used.

Mixing of the crude cyanuric acid and mono-substituted salt to form the resulting slurry as well as the heating stage are achieved by conventional means and procedures. Mixing and heating may be done separately or carried out in a single stage. For example, one procedure to employ when mixing and heating are done separately, is to mix the crude cyanuric acid with water to form a slurry of cyanuric acid, place the slurry in a pressure vessel and heat the vessel to the desired temperature. The salt is then passed into the pressure vessel either as a solid or as an aqueous solution, mixed with the crude cyanuric acid, and the reaction takes place. When mixing and heating are carried out in a single stage process, one procedure to employ is to add the crude cyanuric acid, in either dry, moist or water slurried form to an aqueous salt solution, which is mixed and passed into a reactor which is previously or subsequently heated to the desired temperature. The reaction is then permitted to go to completion. Alternate procedures may likewise be employed.

When the digestion reaction is complete, the hot digested cyanuric acid slurry is cooled to any conventional means to precipitate the cyanuric acid crystals. The crystals are then recovered from the digestion solution by any desirable means. One process that may be employed to recover the cyanuric acid crystals is disclosed in U.S. Pat. No. 3,107,244. In this process, the hot digested cyanuric acid slurry is cooled to a temperature above about 57°C to precipitate anhydrous cyanuric acid crystals. The precipitated crystals are then separated from the digestion solution by filtration at a temperature above about 57°C. The separated crystals are then washed with hot water at a temperature above about 57°C, and the washed cyanuric acid crystals are recovered. Alternative methods for precipitating and recovering cyanuric acid crystals may also be employed.

The recovered cyanuric acid crystals may then be dried and stored, or passed directly to a chlorinator and converted into chloroisocyanuric acids. The conversion of cyanuric acid into chloroisocyanuric acids, such as dichloroisocyanuric acid and/or trichloroisocyanuric acid is well known in the art and does not constitute part of this invention.

Drying may be carried out in any conventional manner in order to remove residual moisture and to produce a freeflowing crystalline product. Preferably, the crystals are dried by heating the crystals with conventional means at a temperature of at least 120°C to the decomposition temperature of the crystals (approximately 300°C).

Removal of the digestion solution from the cyanuric acid crystals results in crystals that can be handled easily and prevents the formation of hard cement-like masses of cyanuric acid. However, removal of all of the digestion solution from the crystals is not commercially feasible. It has been determined that removal of all but residual trace amounts of digestion solution from the crystals produces a commercially satisfactory product. These residual trace amounts of digestion solution remaining on the crystals must generally constitute less than 0.15% by weight, and preferably about 0.001% to about 0.1% by weight phosphate or sulfate values. The phrase "phosphate values" refers to the phosphate salts present in the digestion solution when the amino-substituted triazines are digested with ammonium, sodium or potassium dihydrogen orthophosphate. The phrase "sulfate values" refers to the sulfate salts present in the digestion solution when the amino-substituted triazines are digested with ammonium, sodium or potassium bisulfate.

The separated digestion solution contains the remainder of the dissolved impurities, salt products, and excess monosubstituted salts. The entire digestion solution or portions thereof may be sporadically or continuously recycled to the digester. The portion of the digestion solution not recycled is conveniently used as a source of useful byproducts containing phosphate or sulfate salts. For example, digestion solutions containing diammonium phosphate [$(NH_4)_2HPO_4$] or ammonium sulfate [$(NH_4)_2SO_4$] resulting from the digestion of amino-substituted triazines with ammonium dihydrogen orthophosphate and ammonium bisulfate respectively, may be used directly as a fertilizer, feed additive, or nutrient in fermentation processes. Digestion solutions containing sodium sulfate ($Na_2SO_4$) sodium ammonium sulfate ($NaNH_4SO_4$) and ammonium sulfate [$(NH_4)_2SO_4$] or potassium sulfate ($K_2SO_4$) potassium ammonium sulfate ($KNH_4SO_4$) and ammonium sulfate [$(NH_4)_2SO_4$] resulting from the digestion of amino-substituted triazines with sodium bisulfate and potassium bisulfate respectively, are useful as fertilizers for chloride-sensitive crops such as tobacco and citrus with regard to the potassium salts, and as fillers in synthetic detergents, and textile fiber processes with regard to the sodium salts. Digestion solutions containing disodium phosphate ($Na_2HPO_4$) and sodium ammonium phosphate ($NaNH_4HPO_4$) or dipotassium phosphate ($K_2HPO_4$) and potassium ammonium phosphate ($KNH_4HPO_4$) resulting from the digestion of amino-substituted triazines with sodium dihydrogen orthophosphate and potassium dihydrogen orthophosphate respectively, are both useful as fertilizers, and as sequestrants in food products. The most economical and preferred compound to produce is diammonium phosphate since it can be directly utilized as a solid fertilizer or as a plant nutrient solution. Processes for producing diammonium phosphate containing solutions are well known and are described in the literature.

The process of the invention may be carried out in a batch type manner or continuously with or without recycle. A once-through digestion system is preferable to a recycle system when employing sodium bisulfate, sodium dihydrogen orthophosphate, potassium bisulfate or potassium dihydrogen orthophosphate to digest the amino-substituted triazines. A continuous digestion system with a recycle is preferable to a batch system when employing ammonium bisulfate or ammonium dihydrogen orthophosphate since the amino-substituted triazines are decomposed to cyanuric acid and ammonium sulfate or diammonium phosphate which act as buffers during high temperature digestion.

When employing a continuous digestion system with a recycle, the digestion solution is recycled until the pH of the digestion solution is above about 5.0. Once the digestion solution reaches a pH above about 5.0, the solution is either discarded from the system to yield the useful by-products discussed above, or regenerated and then recycled, even though regeneration may optionally be carried out before the pH is above about 5.0. Digestion solutions containing ammonium sulfate can be recycled seven or eight times before being discarded or regenerated. Regenerated digestion solutions are recycled and mixed with the crude cyanuric acid or amino-substituted triazines and digestion is carried out as described above to yield pure cyanuric acid crystals.

Digestion solutions containing ammonium sulfate are regenerated by adding sufficient amounts of ammonium bisulfate and/or sulfuric acid to the digestion solution to lower the pH of the digestion solution to between 0.2 and 5.0, and preferably between 0.5 and 2.5. The addition of ammonium bisulfate results in lowering the pH and replacing ammonium sulfate with ammonium bisulfate which is the active material digesting the amino-substituted triazines. The addition of sulfuric acid results in lowering the pH and converting ammonium sulfate to ammonium bisulfate according to the following equation:

$$(NH_4)_2SO_4 + H_2SO_4 \rightarrow 2NH_4HSO_4$$

To convert ammonium sulfate to ammonium bisulfate stoichiometric amounts of sulfuric acid are added to the digestion solution, that is one mole of sulfuric acid is added for every mole of ammonium sulfate. Amounts of sulfuric acid above the stoichiometric amount are not required even though the sulfuric acid concentration present in the resulting crude cyanuric acid slurry can be below about 10% and are preferably between about 5% and about 10%. Sulfuric acid concentrations in the resulting slurry must not exceed 10%, since concentrations above 10% will result in extensive corrosion of the digester equipment.

The sulfuric acid is employed as concentrated sulfuric acid (95% to 97%) or as an aqueous sulfuric acid solution prepared from sulfuric acid dispersed in water to any desired sulfuric acid concentration. The exact amount of ammonium bisulfate or sulfuric acid necessary to regenerate the digester solution is readily determined by analyzing the ammonium sulfate or bisulfate concentration in the recovered digestion solution by conventional methods and then adding the required amount of ammonium bisulfate or sulfuric acid to the digester solution to effect regeneration.

When either of these regeneration methods are employed, it is necessary to adjust the regenerated digestion solution salt concentration to below about 30% so that when the regenerated digestion solution is recycled and mixed with the crude cyanuric acid the total salt concentration in the resulting slurry does not exceed about 30%. The regenerated digestion solution salt concentration is conveniently adjusted by either adding water to the regenerated digestion solution or purging a portion of the digestion solution prior to regeneration and adding water to the remaining portion to be regenerated and recycled.

Digestion solutions containing diammonium phosphate are regenerated according to the above procedure to a pH between 0.2 and 5.0 and preferably between 0.5 and 2.5 with either ammonium dihydrogen orthophosphate and/or phosphoric acid. The addition of ammonium dihydrogen orthophosphate results in lowering the pH and replacing diammonium phosphate with ammonium dihydrogen orthophosphate which is the active material digesting the amino-substituted triazines. The addition of phosphoric acid results in lowering the pH and converting diammonium phosphate to ammonium dihydrogen orthophosphate according to the following equation:

$$(NH_4)_2HPO_4 + H_3PO_4 \rightarrow 2NH_4H_2PO_4$$

Amounts of phosphoric acid above the stoichiometric amount are not required even though the phosphoric acid concentration present in the resulting crude cyanuric acid slurry can be between about 10% and about 15%.

Conversion of ammonium sulfate to ammonium bisulfate with sulfuric acid may be performed in situ either during the mixing step whereby the crude cyanuric acid slurry is formed or during the heating step wherein the amino-substituted triazines are being hydrolyzed. The preferred in situ procedure is carried out during mixing wherein an aqueous sulfuric acid solution is mixed with the crude cyanuric acid, the mono-substituted salt and/or the recycled digestion solution to form a 10% to 45% cyanuric acid slurry containing about 5% to about 10% sulfuric acid and about 10% to about 30% of said mono-substituted salt.

Conversion of diammonium phosphate to ammonium dihydrogen orthophosphate with phosphoric acid can also be performed in situ as described above with sufficient amounts of phosphoric acid to form a slurry containing about 10% to about 15% phosphoric acid.

It has been unexpectedly discovered that the amino-substituted triazine conversion rate is almost doubled when the digester slurry contains about 10% to to about 15% phosphoric acid in addition to about 10% to about 30% of the mono-substituted salt of a tribasic phosphate acid. This increase in conversion rate occurs only with slurries containing ammonium dihydrogen orthophosphate, sodium dihydrogen orthophosphate, or potassium dihydrogen orthophosphate. This increase in conversion rate is commercially significant in view of the substantial increase in cyanuric acid yields obtained over a given time period. In addition, this increase in conversion rate is highly significant especially when employing ammonium dihydrogen orthophosphate since not only are the amino-substituted triazines more rapidly converted to cyanuric acid and diammonium phosphate at these high operating temperatures, but the diammonium phosphates formed during the digestion reaction are simultaneously converted to ammonium dihydrogen orthophosphates which further aid in the digestion reaction. Amounts of phosphoric acid above about 15% are not preferred since the conversion rate does not significantly increase with higher phosphoric acid concentrations. The recovered digestion solution is either discarded to produce useful by-products or regenerated and recycled as described above.

The phosphoric acid is employed as concentrated phosphoric acid or as an aqueous phosphoric acid solution prepared from orthophosphoric acid, pyrophosphoric acid, superphosphoric acid or combinations thereof dispersed in water to any desired phosphoric acid concentration.

The cyanuric acid crystals produced according to this invention are novel, large, well-defined, free-flowing crystals. Crystal size has been unexpectedly discovered to be dependent upon the specific digester solution employed. For example, when the digester solution contains ammonium bisulfate, sodium bisulfate, potassium bisulfate, or ammonium dihydrogen orthophosphate and phosphoric acid, at least 90% of the cyanuric acid crystals recovered have particle sizes between 700 and 800 microns and have bulk densities of about 1.10 g/cc and contain about 0.001% to about 0.1% sulfate or phosphate values described above. The crystals are approximately 15 times larger than conventionally prepared cyanuric acid crystals. The direct formation of large crystals permits the crystals to be recovered in an easy and efficient manner without the need for careful controls to prevent cyanuric acid losses formerly attributable to conventional separating equipment. Furthermore, the crystals produced have frangibility values approximately equal to conventionally prepared crystals. This property permits the crystals to be handled, shipped, and stored easily without the difficulties associated with dusting.

The invention will be better understood from a consideration of the following examples. The examples are given to illustrate the invention, and are not deemed to be limiting thereof. All percentages given are based upon total slurry weight unless otherwise indicated.

EXAMPLE 1

This example demonstrates the effect of different inorganic salts on the percentage of amino-substituted triazines converted to cyanuric acid.

INVENTIVE RUN 1

A 25.8 gram (0.2 mole) sample of crude cyanuric acid prepared from urea assaying about 80% cyanuric acid, 18% ammelide, and 2% ammeline was mixed with 50 grams (0.43 moles) of ammonium bisulfate ($Na_4HSO_4$) and 120 grams of water to form a crude cyanuric acid slurry. The slurry was charged into a 300 milliliter Hastelloy B autoclave. The autoclave was sealed, shaken, and heated to 200°C over an 85 minute time period. The reaction temperature was then maintained at 200°C for one minute. The autoclave was then quenched in an ice bath and rapidly cooled to 10°C. The reaction mixture was removed from the autoclave and the crystallized cyanuric acid was filtered from the digestion solution. The filtered cyanuric acid crystals were then analyzed for cyanuric acid, ammelide and ammeline content. The product had a bulk density of about 1.10 g/cc and had at least 90% cyanuric acid crystals with particle sizes between 700 and 800 microns. The results are set forth in Table I.

INVENTIVE RUN 2

The procedure of Run 1 was repeated except that 50 grams (0.36 moles) of sodium bisulfate monohydrate ($NaHSO_4 \cdot H_2O$) was used instead of ammonium bisulfate. The product had a bulk density of about 1.10 g/cc and had at least 90% cyanuric acid crystals with particle sizes between 700 and 800 microns. The results are set forth in Table I.

INVENTIVE RUN 3

The procedure of Run 1 was repeated except that 50 grams (0.43 moles) of ammonium dihydrogen orthophosphate was used instead of ammonium bisulfate. The product had at least 90% cyanuric acid crystals with particle sizes between 300 and 400 microns. The results are set forth in Table I.

COMPARATIVE RUN A

The procedure of Run 1 was repeated except that 50 grams (0.93 moles) of ammonium chloride was used instead of ammonium bisulfate. The product had at least 90% cyanuric acid crystals with particle sizes below 100 microns. The results are set forth in Table I.

EXAMPLE 2

This example demonstrates the percentage conversion of amino-substituted triazines to cyanuric acid with ammonium bisulfate, and ammonium dihydrogen orthophosphate in combination with phosphoric acid. This example also demonstrates the reaction conversion velocity rates.

INVENTIVE RUNS 5 TO 9

A 25.8 gram (0.2 mole) sample of crude cyanuric acid prepared from urea assaying about 80% cyanuric acid, 18% ammelide and 2% ammeline was mixed with 100 milliliters of water to form a 10.8% slurry. The slurry was charged into a 300 milliliter Hastelloy B autoclave. The autoclave was sealed, shaken, and heated to 200°C. A solution of 50 grams ammonium dihydrogen orthophosphate in 61 milliliters of water maintained at 70°C was then blown into the autoclave under pressure either alone or simultaneously with an aqueous phosphoric acid solution. In Run 5, no phosphoric acid was added. In Run 6, 10.46 grams of 86% orthophosphoric acid in 140 grams water was blown into the autoclave. In Run 7, 20.9 grams of 86% orthophosphoric acid in 140 grams water was blown into the autoclave. In Run 8, 23.5 grams of 86% orthophosphoric acid in 140 grams water was blown into the autoclave. In Run 9, 34.8 grams of 86% orthophosphoric acid in 140 grams water was blown into the autoclave. The reaction temperature was maintained at 200°C for 1 minute. The autoclave was then quenched in an ice bath and rapidly cooled to 80°C within 30 seconds. After cooling to 10°C the crystallized cyanuric acid was filtered from the digestion solution. The filtered cyanuric acid crystals were then analyzed for cyanuric acid, ammelide and ammeline content. The results are set forth in Table II. The reaction velocities are set forth in Table II as a rate constant in reciprocal hours under the heading $k \, hr^{-1}$.

INVENTIVE RUN 10

The procedure of Run 5 was repeated except that a solution of 50 grams ammonium bisulfate in 61 milliliters of water maintained at 70°C was blown into the autoclave under pressure instead of the ammonium dihydrogen orthophosphate solution. The results are set forth in Table II.

EXAMPLE 3

This example demonstrates the effect of using recycled ammonium bisulfate digestion solutions to convert aminosubstituted triazines to cyanuric acid.

INVENTIVE RUNS 11 to 18

In Run 11, a 25.8 gram (0.2 mole) sample of crude cyanuric acid prepared from urea assaying about 80% cyanuric acid, 18% ammelide and 2% ammeline was mixed with 50 grams (0.43 moles) of ammonium bisulfate and 120 grams water to form a crude cyanuric acid slurry. The slurry was charged into a 300 milliliter Hastelloy B autoclave. The autoclave was sealed, shaken, and heated to 200°C over an 85 minute time period. The reaction temperature was maintained at 200°C for one minute. The autoclave was then quenched in an ice bath and rapidly cooled to 10°C. The reaction mixture was removed from the autoclave and the crystallized cyanuric acid was filtered from the digestion solution. The filtered cyanuric acid crystals were then analyzed for cyanuric acid, ammelide and ammeline content.

In Run 12, the original combined weight (170 grams) of ammonium bisulfate and water was restored by adding 11 grams of water to the recovered digestion solution of Run 11 which weighed 159 grams. A 25.8 gram (0.2 mole) sample of crude cyanuric acid prepared as above and assaying 80% cyanuric acid, 18% ammelide, and 2% ammeline was added to the restored solution and treated according to Run 11. The cyanuric acid crystals were filtered from the digestion solution and analyzed for cyanuric acid, ammelide and ammeline content. The procedure of Run 12 was repeated in Runs 13 and 14 with the recovered digestion solutions of Runs 12 and 13 respectively.

In Run 14R, the recovered digestion solution from Run 14 was regenerated with sulfuric acid. The digestion solution was analyzed for ammonium sulfate content [$(MH_4)_2SO_4$]. A stoichiometric amount of concentrated sulfuric acid (95% sulfuric acid) was then added to the digestion solution to convert ammonium sulfate to ammonium bisulfate. A 35% portion of the digestion solution was purged and water was added to the digestion solution to restore the ammonium bisulfate and water content to 170 grams.

In Run 15, the regenerated digestion solution (Run 14R) was mixed with crude cyanuric acid according to Run 11 and the filtered cyanuric acid crystals analyzed for cyanuric acid, ammelide, and ammeline content.

In Runs 16, 17 and 18 the procedure of Run 12 was repeated with the recovered digestion solutions from Runs 15, 16 and 17 respectively, and the filtered cyanuric acid crystals analyzed for cyanuric acid, ammelide, and ammeline content.

All results are set forth in Table III.

The invention being thus described, it will be obvious that the same may be varied in many ways. Such variations are not to be regarded as a departure from the spirit and scope of the invention, and all such modifications are intended to be included within the scope of the following claims.

TABLE I

| Run No. | Inorganic Salt | Reaction pH Starting | Reaction pH Final | Product Analysis % Cyanuric Acid | Product Analysis % Ammelide and Ammeline | Total % of Ammelide & Ammeline Conversion | Cyanuric Acid Crystal Size |
|---|---|---|---|---|---|---|---|
| 1 | $NH_4HSO_4$ | 0.50 | 0.65 | >99.9 | trace | 99 | >90% particle sizes between 700 and 800 microns |
| 2 | $NaHSO_4 \cdot H_2O$ | 0.80 | 1.05 | >99.9 | trace | 99 | same as Run 1 |
| 3 | $NH_4H_2PO_4$ | 4.15 | 4.4 | >99.9 | trace | 97 | >90% particle sizes between 300 and 400 microns |
| 4 | $NaH_2PO_4 \cdot H_2O$ | 4.25 | 4.95 | 99.2 | 0.8 | 95 | >90% particle sizes between 200 and 300 microns |
| Comparative A | $NH_4Cl$ | 4.81 | 5.8 | 84.4 | 15.6 | 26 | >90% particle sizes less than 100 microns |

">" means greater than.

TABLE II

| Run No. | $NH_4HSO_4$ Concentration in % | $NH_4H_2PO_4$ Concentration in % | $H_3PO_4$ Concentration in % | Final Reaction pH | Total % of Ammelide & Ammeline Conversion | k hr$^{-1}$ | Cyanuric Acid Crystal Size |
|---|---|---|---|---|---|---|---|
| 5 | 0 | 21.0 | 0 | 4.95 | 83.0 | 78 | >90% particle sizes between 300 and 400 microns |
| 6 | 0 | 21.0 | 6.0 | 3.35 | 88.1 | 127 | Same as Run 5 |
| 7 | 0 | 21.0 | 12.5 | 2.45 | 97.8 | 228 | >90% particle sizes between 700 and 800 microns |
| 8 | 0 | 21.0 | 13.9 | 2.42 | 97.5 | 226 | Same as Run 7 |
| 9 | 0 | 21.0 | 20.0 | 2.25 | 97.8 | 228 | Same as Run 7 |
| 10 | 21.0 | 0 | 0 | 0.65 | 95.0 | 180 | Same as Run 7 |

">" means greater than.

TABLE III

| Run No. | Reaction pH Starting | Reaction pH Final | Product Analysis % Cyanuric Acid | % Ammelide & Ammeline | Total % of Ammelide % Ammeline Conversion | Remarks |
|---|---|---|---|---|---|---|
| 11 | 0.50 | 0.55 | >99.9 | trace | 99.0 | Digestion with fresh solution |
| 12 | 0.55 | 0.65 | >99.9 | trace | 98.9 | Digestion with first recycle solution from Run 11 |
| 13 | 0.65 | 0.95 | >99.9 | trace | 98.9 | Digestion with second recycle solution from Run 12 |
| 14 | 0.95 | 1.25 | >99.9 | trace | 98.5 | Digestion with third recycle solution from Run 13 |
| 14R | Regeneration of Run 14 digestion solution | | | | | |
| 15 | 0.50 | 0.56 | >99.9 | trace | 99.0 | Digestion with Run 14 regenerated digestion solution |
| 16 | 0.56 | 0.67 | >99.9 | trace | 98.9 | Digestion with recycle solution from Run 15 |
| 17 | 0.67 | 0.98 | >99.9 | trace | 98.8 | Digestion with recycle solution from Run 16 |
| 18 | 0.98 | 1.27 | >99.9 | trace | 98.5 | Digestion with recycle solution from Run 17 |

">" means greater than.

What is claimed is:

1. A process for purifying crude cyanuric acid, which comprises:
   a. mixing in water sufficient amounts of crude cyanuric aciid and a mono- salt of an inorganic acid, wherein said inorganic acid is a dibasic or tribasic inorganic acid capable of forming a salt with a material selected from the group consisting of ammonium, potassium, sodium, lithium, rubidium, and cesium, wherein said salt contains the acid radical and one or more unreacted hydrogen atoms, to form a 10% to 45% crude cyanuric acid slurry containing about 10% to about 30% mono- salt of an inorganic acid;
   b. heating the slurry to a temperature of about 160°C to about 220°C under at least the autogenously developed pressure to digest the crude cyanuric acid impurities;
   c. cooling the digested cyanuric acid slurry to precipitate the cyanuric acid crystals; and
   d. recovering the cyanuric acid crystals from the digestion solution.

2. The process of claim 1 wherein said mono- salt of an inorganic acid is selected from the group consisting of ammonium bisulfate, ammonium dihydrogen orthophosphate, sodium bisulfate, sodium dihydrogen orthophosphate, potassium bisulfate, and potassium dihydrogen orthophosphate.

3. The process of claim 1 wherein sufficient amounts of crude cyanuric acid are mixed with a mono- salt of an inorganic acid to form a 10% to 25% crude cyanuric acid slurry.

4. The process of claim 1 wherein the crude cyanuric acid impurities are digested for about 15 seconds to about 10 minutes.

5. The process of claim 1, wherein the slurry is heated to a temperature of about 190°C to about 205°C.

6. The process of claim 1 wherein mixing step (a) and heating step (b) are carried out in a single stage.

7. The process of claim 1 wherein the mono- salt of an inorganic acid is ammonium bisulfate.

8. The process of claim 7 wherein the recovered cyanuric acid product contains at least 90% cyanuric acid crystals having particle sizes between 700 and 800 microns.

9. The process of claim 1 wherein the mono- salt of an inorganic acid is sodium bisulfate.

10. The process of claim 9 wherein the recovered cyanuric acid product contains at least 90% cyanuric acid crystals having particle sizes between 700 and 800 microns.

11. The process of claim 1 wherein the mono- salt of an inorganic acid is potassium bisulfate.

12. The process of claim 11 wherein the recovered cyanuric acid product contains at least 90% cyanuric acid crystals having particle sizes between 700 and 800 microns.

13. The process of claim 1 wherein the recovered cyanuric acid crystals of step (d) are dried at a temperature of at least 120°C to the decomposition temperature of the crystals.

14. The process of claim 1 which comprises: recycling the recovered digestion solution from step (d) to step (a) to provide a mono- salt of an inorganic acid to purify the crude cyanuric acid.

15. The process of claim 1 which comprises: recycling the recovered digestion solution from step (d) to step (a) until the pH of the recovered digestion solution is above about 5.0 to provide a mono- salt of an inorganic acid to purify the crude cyanuric acid.

16. The process of claim 1 wherein the digestion solution of step (d) containing a mono- salt of an inorganic acid selected from the group consisting of ammonium bisulfate, and ammonium dihydrogen orthophosphate and having a pH between 0.2 and 5.0 is recycled is step (a) to provide said mono- salt of an inorganic acid to purify the crude cyanuric acid.

17. The process of claim 1 which comprises: regenerating the recovered digestion solution by adjusting the pH of the recovered digestion solution to between 0.2 and 5.0 with a material selected from the group consisting of (1) a mono- salt of an inorganic acid identical to the mono- salt of the inorganic acid used in step (a) and (2) a molecular acid from which the mono- salt of the inorganic acid was derived, recycling the regenerated digestion solution to step (a) to provide a mono- salt of an inorganic acid to purify the crude cyanuric acid, and mixing the regenerated digestion solution with the crude cyanuric acid.

18. The process of claim 1 which comprises: regenerating the recovered digestion solution of step (d) containing ammonium sulfate by adjusting the pH of said digestion solution to between 0.2 and 5.0 with a material selected from the group consisting of ammonium bisulfate, and sulfuric acid, recycling the regenerated digestion solution to step (a) to provide a mono- salt of an inorganic acid to purify the crude cyanuric acid, and mixing the regenerated digestion solution with the crude cyanuric acid.

19. The process of claim 1 which comprises: regenerating the recovered digestion solution of step (d) containing diammonium phosphate by adjusting the pH of said digestion solution to between 0.2 and 5.0 with a material selected from the group consisting of ammonium dihydrogen orthophosphate, and phosphoric acid, recycling the regenerated digestion solution to step (a) to provide a mono- salt of an inorganic acid to purify the crude cyanuric acid, and mixing the regenerated digestion solution with the crude cyanuric acid.

20. The process of claim 1, wherein the crude cyanuric acid of step (a) is mixed with water, an aqueous sulfuric acid solution, and a mono- salt of a dibasic inorganic acid selected from the group consisting of ammonium bisulfate, sodium bisulfate, and potassium bisulfate to form a 10% to 45% crude cyanuric acid slurry containing about 5% to about 10% sulfuric acid and about 10% to about 30% of said mono- salt of a dibasic inorganic acid.

21. The process of claim 1, wherein the crude cyanuric acid of step (a) is mixed with water, an aqueous phosphoric acid solution, and a mono- salt of a tribasic inorganic acid selected from the group consisting of ammonium dihydrogen orthophosphate, sodium dihydrogen orthophosphate, and potassium dihydrogen orthophosphate to form a 10% to 45% crude cyanuric acid slurry containing about 10% to about 15% phosphoric acid and about 10% to about 30% of said mono- salt of a tribasic inorganic salt.

22. The process of claim 21 wherein the mono- salt of a tribasic inorganic acid is ammonium dihydrogen orthophosphate and the recovered cyanuric acid product contains at least 90% cyanuric acid crystals having particle sizes between 700 and 800 microns.

23. The process of claim 1 wherein said mono- salt is employed in amounts of at least 10% over the stoichiometric amount.

24. A process of purifying crude cyanuric acid, which comprises:
   a. mixing in water sufficient amounts of crude cyanuric acid, an aqueous sulfuric acid solution, and a mono- salt of a dibasic inorganic acid selected from the group consisting of ammonium bisulfate, sodium bisulfate and potassium bisulfate to form a 10% to 45% crude cyanuric acid slurry containing about 5% to about 10% sulfuric acid and about 10% to about 30% of said mono- salt of a dibasic inorganic acid;
   b. heating the slurry for about 15 seconds to about 10 minutes to a temperature of about 160°C to about 220°C under at least the autogenously developed pressure to digest the crude cyanuric acid impurities;
   c. cooling the digested cyanuric acid slurry to precipitate the cyanuric acid crystals; and
   d. recovering the cyanuric acid crystals from the digestion solution.

25. The process of claim 24, which comprises recycling the recovered digestion solution from step (d) to step (a) until the pH value of the digestion solution is above about 5.0 to provide a mono- salt of an inorganic acid.

26. A process for purifying crude cyanuric acid, which comprises:
   a. mixing in water sufficient amounts of crude cyanuric acid and a mono- salt of an inorganic acid selected from the group consisting of ammonium bisulfate, ammonium dihydrogen orthophosphate, sodium bisulfate, sodium dihydrogen orthophosphate, potassium bisulfate and potassium dihydrogen orthophosphate, to form a 10% to 25% crude cyanuric acid slurry containing about 10% to about 30% of said mono- salt of an inorganic acid;
   b. heating the slurry for about 15 seconds to about 10 minutes at a temperature of about 190°C to about 205°C under at least the autogenously developed pressure to digest the crude cyanuric acid impurities;
   c. cooling the digested cyanuric acid slurry to precipitate the cyanuric acid crystals; and
   d. recovering the cyanuric acid crystals from the digestion solution.

27. The process of claim 26 wherein mixing step (a) and heating step (b), are carried out in a single stage.

28. A process for purifying crude cyanuric acid which comprises:
   a. mixing in water sufficient amounts of crude cyanuric acid and a mono- salt of a dibasic inorganic acid selected from the group consisting of ammonium bisulfate, sodium bisulfate and potassium bisulfate, to form a 10% to 25% crude cyanuric acid slurry containing about 10% to about 30% of said mono- salt of a dibasic inorganic acid;
   b. heating the slurry for about 15 seconds to about 10 minutes at a temperature of about 190°C to about 205°C under at least the autogenously developed pressure to digest the crude cyanuric acid impurities;
   c. cooling the digested cyanuric acid slurry to precipitate the cyanuric acid cyrstals; and
   d. recovering the cyanuric acid crystals from the digestion solution wherein at least 90% of the cyanuric acid crystals have particle sizes between 700 and 800 microns.

29. The process of claim 28 wherein mixing step (a) and heating step (b) are carried out in a single stage.

30. A process for purifying crude cyanuric acid which comprises:
   a. mixing in water sufficient amounts of crude cyanuric acid, an aqueous phosphoric acid solution, and a mono- salt of a tribasic inorganic acid selected from the group consisting of ammonium dihydrogen orthophosphate, sodium dihydrogen orthophosphate, and potassium dihydrogen orthophosphate, to form a 10% to 25% crude cyanuric acid slurry containing about 10% to about 15% phosphoric acid and about 10% to about 30% of said mono- salt of a tribasic inorganic acid;
   b. heating the slurry for about 15 seconds to about 10 minutes at a temperature of about 190°C to about 205°C under at least the autogenously developed pressure to digest the crude cyanuric acid impurities;
   c. cooling the digested cyanuric acid slurry to precipitate the cyanuric acid crystals; and
   d. recovering the cyanuric acid crystals from the digestion solution.

31. The process of claim 30 wherein the mono- salt of a tribasic inorganic acid is ammonium dihydrogen orthophosphate and the recovered cyanuric acid product contains at least 90% cyanuric acid crystals having particle sizes between 700 and 800 microns.

32. The process of claim 30 wherein mixing step (a) and heating step (b) are carried out in a single stage.

33. A process for purifying crude cyanuric acid, which comprises:
   a. mixing in water sufficient amounts of crude cyanuric acid and ammonium bisulfate to form a 10% to 45% crude cyanuric acid slurry containing about 10% to about 30% ammonium bisulfate;
   b. heating the slurry for about 15 seconds to about 10 minutes at a temperature of about 160°C to about 220°C under at least the autogenously developed pressure to digest the crude cyanuric acid impurities;
   c. cooling the digested cyanuric acid slurry to precipitate the cyanuric acid crystals;
   d. recovering the cyanuric acid crystals from the digestion solution;
   e. recycling the recovered digestion solution from step (d) to step (a) until the pH of the digestion solution is above about 5.0 to provide a mono- salt of an inorganic acid; and
   f. mixing the recycled digestion solution with the crude cyanuric acid in step (a) to purify the crude cyanuric acid.

34. The process of claim 33 which comprises maintaining the pH of the recycled digestion solution of step (e) between 0.2 and 5.0 with a material selected from the group consisting of ammonium bisulfate, and sulfuric acid.

35. The process of claim 34 wherein the pH of the recycled digestion solution is maintained between 0.5 and 2.5.

36. The process of claim 33 which comprises drying the recovered cyanuric acid crystals from step (d) at a temperature of at least 120°C to the decomposition temperature of the crystals.

37. The process of claim 33 wherein mixing step (a), and heating step (b), are carried out in a single stage.

38. A process for purifying crude cyanuric acid, which comprises:
   a. mixing in water sufficient amounts of crude cyanuric acid, an aqueous phosphoric acid solution, and ammonium dihydrogen orthophosphate to form a 10% to 45% crude cyanuric acid slurry containing about 10% to about 15% phosphoric acid and about 10% to about 30% ammonium dihydrogen orthophosphate;
   b. heating the slurry for about 15 seconds to about 10 minutes at a temperature of about 190°C to about 205°C under at least the autogenously developed pressure to digest the crude cyanuric acid impurities;
   c. cooling the digested cyanuric acid slurry to precipitate the cyanuric acid crystals;
   d. recovering the cyanuric acid crystals from the digestion solution;
   e. recycling the recovered digestion solution from step (d) to step (a) until the pH of the digestion solution is above about 5.0 to provide a mono- salt of an inorganic acid; and
   f. mixing the recycled digestion solution with the crude cyanuric acid in step (a) to purify the crude cyanuric acid.

39. The process of claim 38 which comprises maintaining the pH of the recycled digestion solution of step (e) between 0.2 and 5.0 with a material selected from the group consisting of ammonium dihydrogen orthophosphate, and phosphoric acid.

40. The process of claim 39 wherein the pH of the recycled digestion solution is maintained between 0.5 and 2.5.

41. The process of claim 38 which comprises drying the recovered cyanuric acid crystals from step (d) at a temperature of at least 120°C to the decomposition temperature of the crystals.

42. The process of claim 38 wherein mixing step (a) and heating step (b) are carried out in a single stage.

43. A process for making cyanuric acid, which comprises:
   forming an aqueous mixture of an amino-substituted triazine compound selected from the group consisting of melamine, ammeline, ammelide, ammeline: ammelide complex and mixtures thereof with a mono- salt of an inorganic acid wherein said inorganic acid is a dibasic or tribasic inorganic acid capable of forming a salt with a material selected from the group consisting of ammonium, potassium, sodium, lithium, rubidium, and cesium, wherein said salt contains the acid radical and one or more unreacted hydrogen atoms, in amounts sufficient to furnish at least stoichiometric amounts of said mono- salt to the amine substitutes of said compounds;
   heating said mixture to a temperature of about 160°C to about 220°C under at least the autogenously developed pressure to digest the amino-substituted triazine,
   cooling said mixture to precipitate the cyanuric acid crystals; and
   recovering the cyanuric acid crystals from the digestion solution.

44. The process of claim 43 wherein said mono- salt is employed in amounts of at least 10% over the stoichiometric amount.

45. The process of claim 43 wherein said mono- salt is selected from the group consisting of ammonium bisulfate, ammonium dihydrogen orthophosphate, sodium bisulfate, sodium dihydrogen orthophosphate, potassium bisulfate, and potassium dihydrogen orthophosphate.

* * * * *

UNITED STATES PATENT OFFICE
CERTIFICATE OF CORRECTION

PATENT NO. : 3,969,352
DATED : July 13, 1976
INVENTOR(S) : SIDNEY BERKOWITZ

It is certified that error appears in the above-identified patent and that said Letters Patent are hereby corrected as shown below:

Column 5, line 11 "to" should read --by--.

Column 6, line 7 "($Na_2SO_4$)" should read --($Na_2SO_4$),--.

Column 6, line 9 "($K_2SO_4$)" should read --($K_2SO_4$),--.

Column 8, line 13 "to to" should read --to--.

Column 8, line 55 "The" should read --These--.

Column 10, line 37 "aminosubstituted" should read --amino-substituted--.

Column 12, Table III "Total % of Ammelide % Ammeline Conversion" should read --Total % of Ammelide & Ammeline Conversion--.

Column 13, line 5 "aciid" should read --acid--.

Signed and Sealed this

First Day of March 1977

[SEAL]

Attest:

RUTH C. MASON
Attesting Officer

C. MARSHALL DANN
Commissioner of Patents and Trademarks